United States Patent [19]

Baniel et al.

[11] 4,275,234

[45] Jun. 23, 1981

[54] RECOVERY OF ACIDS FROM AQUEOUS SOLUTIONS

[75] Inventors: Avraham M. Baniel; Ruth Blumberg; Klara Hajdu, all of Haifa, Israel

[73] Assignee: Imi (Tami) Institute for Research and Development, Haifa, Israel

[21] Appl. No.: 365,506

[22] Filed: May 31, 1973

[30] Foreign Application Priority Data

Jun. 19, 1972 [IL] Israel .................................. 39710

[51] Int. Cl.³ ........................................ C07C 59/265
[52] U.S. Cl. ............................................ 562/584
[58] Field of Search .......................... 260/535 R, 538

[56] References Cited

U.S. PATENT DOCUMENTS

| | | | |
|---|---|---|---|
| 2,880,179 | 3/1959 | Comar | 260/535 X |
| 3,944,606 | 3/1970 | Rieger et al. | 260/535 P |

OTHER PUBLICATIONS

Vogel; Textbook of Practical Organic Chemistry, 3rd edition, pp. 122-125.

*Primary Examiner*—Paul J. Killos
*Attorney, Agent, or Firm*—Kirschstein, Kirschstein, Ottinger & Cobrin

[57] ABSTRACT

Acids are recovered from their aqueous solution by an extraction process comprising a first extraction stage at which the aqueous solution is contacted with a water-immiscible extractant comprising a water-immiscible organic solvent and, dissolved therein, at least one secondary or tertiary amine in which the aggregate number of carbon atoms is at least 20; and a back-extraction stage in which the organic extract, separated from the original aqueous solution, is stripped with an aqueous liquid at a temperature which is higher by at least 20° C. than the temperature of the first extraction stage. The stripped extractant can be recycled to the first extraction stage for making the process continuous, and if so recycled, is cooled on its way to the extraction stage. A preferred field of application is the recovery of organic acids produced by fermentation from the fermentation broth, e.g. citric acid.

19 Claims, No Drawings

RECOVERY OF ACIDS FROM AQUEOUS SOLUTIONS

This invention concerns the recovery of acids from aqueous solutions.

The recovery of acids from aqueous solutions is necessary in various technical fields. Thus, for example, certain organic acids which are the fermentation products produced by various microorganisms in aqueous nutrient media have to be recovered in as pure and concentrated a state as possible from the fermentation broth. This applies, for example, to citric acid, lactic acid and certain antibiotics such as penicillin. In other cases, it would be desirable to recover acids from industrial effluents where such recovery presents an economic advantage.

In a general manner, there exist several methods for recovering acids from aqueous liquors;
- (a) Precipitation by the formation of sparingly soluble salts, and subsequent decomposition of the latter;
- (b) Extraction with organic solvents which are partly or wholly immiscible with water, such as certain aliphatic alcohols, ketones, ethers or the like;
- (c) Extraction with water-insoluble amines, as a rule dissolved in a substantially water-immiscible organic solvent, followed by the decomposition of the amine salt thus formed with an acid or a base;
- (d) Extraction with amine salts. This is a variant of the extraction with amines mentioned in the preceding paragraph. In some cases the amount of acid that can be extracted with the aid of water-immiscible amine is stoichiometrically considerably in excess of the amine present in the amine solution. The possible excess amount of extracted acid depends on several parameters, e.g. the concentration of the acid in the aqueous solution from which the acid is to be extracted and the nature of the amine and of its solvent. In several cases this phenomenon has been applied for extracting acids from their concentrated aqueous solutions by means of salts of amines with the same acids. From the extract the excess of acid can be recovered by washing with water or, in the case of volatile acids, by distillation.

Precipitation of salts is a straightforward method but cannot be practised in many cases.

The extraction with organic solvents is practised, for example, in the recovery of phosphoric acid from the sludges produced by the acidulation of rock phosphate with sulfuric or hydrochloric acid, and for the purification of crude phosphoric acid. It is useful in many cases, but it presupposes that the acid has a relatively high concentration in the aqueous system from which it is to be extracted.

The extraction by mean of amines has the advantage of providing a favourable coefficient of distribution of the acids between the aqueous and amine phases in the extracting operation, owing to which the acid can be extracted even from highly dilute solutions. On the other hand, there arises the problem of decomposing the amine salt and recovering the acid and the amine separately, since amines are much too expensive to be thrown out. As a rule, the amine is liberated by treatment of the salt with an inorganic base, e.g. calcium hydroxide, and a salt is thus obtained instead of the free acid. In addition to the expenditure of chemicals, this process has the disadvantage of requiring a number of processing steps. In the case of lower amines, it has also been suggested to liberate the amine from the amine salt by steam distillation whereby the salt is decomposed and the amine is at the same time distilled off. This method is not applicable to amines of higher molecular weight, which are the preferred ones for the extraction of the acid from the aqueous system. Also, for a specific case, where sulfuric acid is contained in an aqueous system together with ions of common metals, in particular iron, it has been suggested that if the sulfuric acid is extracted from this specific aqueous system by means of certain tertiary amines of specific structure in which the nitrogen atom is connected to three methylene groups bearing alkyl radicals having branching on the carbon atom nearest the nitrogen atom, and/or aryl radicals, the amine sulfate contained in the solvent extract can be decomposed by treatment with water and the latter strips the solvent extract from liberated sulfuric acid. Other amines not of the structure specified (such as tri-iso-octyl amine) cannot be used.

The extraction with amine salts, too, presupposes that the acid has a relatively high concentration in the aqueous system from which it is to be extracted. Consequently this method has been suggested particularly for purposes such as the recovery of volatile acids from relatively concentrated aqueous solutions thereof.

This invention has the object to provide a process for the extraction of acids from aqueous systems by means of solutions of high-molecular-weight amines in organic solvents, in which the extraction of the acid takes place with a high degree of selectivity even from highly dilute systems, the acid can readily be recovered from the solution of the amine salt in the organic solvent, and if desired, the solution of the amine in the organic solvent can be recycled for the extraction of more acid from the aqueous system.

The invention, accordingly, consists in a process for the extraction of acids from aqueous solutions, comprising an extraction operation in which a water-immiscible organic extractant comprising at least onee secondary or tertiary amine, in which the aggregate number of carbon atoms is at least 20, or a mixture of two or more such amines, dissolved in a water-immiscible organic solvent, is contacted with the aqueous solution of the acid, the organic extract is separated from the residual aqueous liquid and, at a temperature higher than the temperature at which the extraction is performed, subjected to a stripping operation with an aqueous liquid for back-extracting at least a substantial part of the acid from the organic extract into the water and leaving substantially all the amine in the organic phase; the aqueous back-extract is separated from the organic phase.

For the sake of brevity the following terms are used herein "Extractant" means the mixture of amine and solvent. "Extract" means the organic phase comprising the extractant and the acid extracted by the extractant from the original aqueous solution of the acid. "Back-extract" means the aqueous solution of the acid produced by stripping the acid from the extract.

As amines there may be used aliphatic, araliphatic or aromatic amines, or mixed aliphatic-araliphatic or aliphatic-aromatic amines, or mixtures of such amines.

Where mixtures of two or more amines are used, e.g. commercial trialkylamines which contain as a rule some amount of secondary alkylamines, it is sufficient, for the purpose of this invention, if the average aggregate number of carbon atoms is at least 20 for each amino group of the amines.

Amines having altogether less than 20 carbon atoms in the molecule are less suitable for use in the process according to the invention. Such amines as well as their salts with the acids to be extracted are less soluble in the solvent phase and too much soluble in the aqueous phase, hence they tend to dissolve in the aqueous acid solution from which the acid is to be extracted, and to the extent that extraction takes place the amine salts tend to crystallize from the solvent extract.

The process according to the invention can advantageously be performed as a continuous process. In this case the solvent from which the extracted acid has been recovered by back-extraction, is recycled as an extractant and, before or while being thus recycled, is cooled, or allowed to cool, to the temperature at which the extraction is being performed. On the other hand, especially in small-scale operation, the process may be carried out as a batch process in which a batch of the aqueous acid solution is subjected to one or a few extracting operations. If in that case the solvent, from which the extracted acid has been recovered, is recycled for a second, third or even fourth extracting operation, the solvent need not necessarily be cooled before being contacted again with the acid solution, since a gradual rise of the temperature at which the extraction takes place, can in some cases be tolerated.

The concepts of "lower temperature" and "higher temperature" are not understood in absolute terms. What matters for the purposes of this invention is the temperature differential. This will have to be at least 20 degrees (centigrade), both for operational convenience and in order to make both the extraction and the back-extraction as complete as possible. The extraction may be carried out at temperatures as low as near the freezing point of the aqueous acid solution, and the temperature of the back-extraction may be at or near the boiling point of the extract or the water at atmospheric pressure, or if the back-extraction is carried out under elevated pressure, at an even higher temperature, always on condition that the temperature and pressure are so chosen that the amine remains in the organic phase. In many cases the extraction can be carried out at or near room temperature, and the stripping operation at a temperature of about 20 to 40 degrees (centigrade) above room temperature. As a rule the stripping operation is the more effective, the higher the stripping temperature, but the extraction and stripping temperatures will be selected in individual cases in accordance with practical factors such as corrosion resistance and costs of the equipment, costs of heating and cooling of the streams of the acid solution, the extract and the extractant, the required concentration of stripped acid etc.

If the aqueous liquid used for stripping the extract is water, the back-extract is an aqueous solution of the free acid. If desired the back-extracting operation may be so conducted that the back-extract is an aqueous solution of a salt of the extracted acid. For example, back-extraction with an aqueous alkali metal (in this context "alkali metal" includes ammonium) hydroxide solution yields an aqueous solution of the corresponding alkali metal salt of the extracted acid. Or the aqueous back-extracting liquid may be, for example, an alkali metal chloride solution. In this case, too, the back-extract contains the corresponding alkali metal salt of the extracted acid while the amine in the extractant is converted into its hydrochloride. This will thus have to be decomposed, e.g. by treatment with calcium hydroxide, for reconstituting the extractant. Sometimes it is advantageous to perform first a back-extraction with water in order to recover the major part of the acid in the free state. The residue of acid remaining in the solvent extract can then be back-extracted with an alkali metal hydroxide or salt solution.

The most favourable selection of the temperature of the extracting operation and of the compositions of the extractant as regards both the amine and the solvent will also be determined according to the given condition of particular cases, e.g. the kind of acid, its concentration in the original aqueous solution, and impurities present in that solution. The major aim in both the extracting and stripping operations will be to achieve as favourable a distribution coefficient as possible for the distribution of the acid between the aqueous and organic phases. In the extraction operation, this has to be in favour of the extractant, in the stripping operation, in favour of the aqueous phase.

Before the extract is subjected to the stripping operation it may in some cases be desirable to change its composition in order to render the stripping more efficacious. Thus, it may in some cases be desirable to remove some amount of solvent, e.g. by distillation in vacuo; to add some solvent, either the same as forms part of the extractant, or a different one; or both to remove at least some of the extractant solvent and to replace it with a different solvent; or to add other auxiliary substances that may serve to facilitate the back-extraction of the product acid into the aqueous phase.

After the stripping operation the stripped extract may be subjected to such operations as may be required or desired for purifying it or changing or reconstituting its composition, e.g. by the removal of retained impurities or of by-product acids co-extracted with the main product acid and not accompanying the latter into the aqueous back-extract, the removal of a second solvent or of auxiliary substances that may have been added to the extract before the stripping operation; the addition of make-up solvent and/or amine, cooling, and the like.

A technical field for which the present invention is of particular interest is the recovery of citric acid from its fermentation broths. These liquors contain large amounts of organic and some inorganic impurities. Present techniques for the recovery and purification of citric acid have not proceeded beyond the classical steps of precipitating calcium citrate from the broth by the addition of calcium hydroxide, separating the calcium citrate, decomposing it with sulfuric acid, removing the aqueous solution of citric acid from the precipitated calcium sulfate and afterwards evaporating the water and purifying the still rather impure citric acid by a number of successive operations such as selective precipitation, ion exchange, treatment with active carbon, etc. This entire process is not only expensive in view of the plurality of operations and the expenditure of chemicals and energy, but also wasteful owing to significant losses of yield. The situation is hardly better in regard to other fermentation processes, e.g. for the manufacture of lactic acid. Suggestions to the effect that organic acids may be recovered from the aqueous solutions, in particular from fermentation broths, with the aid of long-chain aliphatic amines have been made in the literature but have apparently not yet found application in industrial practice.

In the process according to the invention, various water-immiscible organic solvents, both non-polar and polar, can be used for the extractant, for example, aliphatic and aromatic hydrocarbons, petroleum fractions, hydrocarbons carrying nitro or halo substituents, alcohols or the like, alone or in mixtures. Certain commercial tertiary straight-chain or branched-chain alkylamines in which each alkyl group has from 8 to 13 carbon atoms, or mixtures thereof with secondary amines containing similar alkyl groups, have been found to be particularly satisfactory for the purpose of the process, e.g. tri-n-caprylylamine, tri-n-laurylamine, tri-tridecylamine (with branched alkyl groups) and the like. Similarly, commercial secondary amines in which one of the hydrocarbyl groups has at least 12 carbon atoms and the second one at least 8 carbon atoms, e.g. Amberlite LA-1, have been found suitable.

In general it is found that no, or almost no water dissolves in the extractant, and vice versa. It is also found that in the back-extract the acid is as a rule at least as concentrated as it is in the original aqueous solution from which it has been extracted, and in many cases even more concentrated. The process according to the invention can thus be used in order both to purify and to concentrate the acid. In the case of citric acid, the back-extract is so pure that food-grade citric acid can directly be recovered from it.

The extraction operation will as a rule be performed as a multi-stage continuous counter-current process and the stripped extractant will continuously be recycled to the extraction, being cooled on the way back.

The invention is illustrated by the following examples:

EXAMPLE 1

Crude broth from the citric acid fermentation of sucrose was extracted at ambient temperature in three separatory funnels in simulation of a three-stage counter-current extraction system, each funnel being supplied in turn with portions of 100 g of the broth and 148 g of an extractant composed of 50% w/w of tri-tridecylamine and 50% w/w of xylene. Samples of the extracts and raffinates from the three-stage system were analysed until two successive samples showed substantially identical analysis which indicated that steady state had been reached. The operation was continued, combining the steady-state extracts containing 10% by weight of citric acid, until enough extract had been collected to permit a similar exercise in stripping. The stripping was performed at 80° C., also in a 3-stage separatory funnel system, with 1 part by weight of water for every 2.5 parts of extract feed. At steady state, every 100 g of the original crude broth yielded 80 g of a pure back-extract containing 20% w/w of citric acid.

EXAMPLE 2

100 g of a similar crude citric acid broth as used in Example 1 were extracted at 25° C. in two counter-current stages (simulated by two separatory funnels) with 120 g of an extractant containing 50% w/w of trilaurylamine and 50% w/w of xylene.

The extract amounted to 136 g and contained 12% w/w of citric acid. It was diluted with a further 60 g of xylene and then stripped at 80° C. in three simulated counter-current stages with 38 g of $H_2O$ to yield 55 g of a back-extract containing about 16 g of pure citric acid, i.e. a purified aqueous solution containing 29% w/w of citric acid as compared to 16.4% in the crude feed. After the back-extraction the extractant phase amounted to 180 g. It contained 33% w/w of trilaurylamine and 67% w/w of xylene and was practically free from citric acid. 60 g of xylene were removed therefrom by distillation. The distillation residue of 120 g was reconstituted extractant which was ready for recycling.

EXAMPLE 3

The extraction of the crude citric acid broth was carried out as described in Example 2. The extract, 136 g containing 12% w/w of citric acid, was heated with 80 g of $H_2O$ to 140° C., in an adapted Carius pressure vessel. A sample, taken under pressure through a tube dipping into the aqueous back-extract phase, showed that the latter contained 14% w/w of citric acid. Accordingly the total amount of citric acid in the back-extract was 13 g.

This Example showed that if the back-extraction was effected at an elevated temperature under pressure, it was not necessary to dilute the extract before the back-extraction. Accordingly no diluent had to be removed before the extractant was recycled.

EXAMPLE 4

100 g of a 12.8% w/w crude citric-acid broth were extracted at 25° C. in four counter-current stages with 145 g of extractant containing 25% w/w of technical-grade trioctylamine and 75% w/w of a petroleum fraction boiling at 140°–210° C. A three-phase system, viz. an aqueous phase and two organic extract phases, was formed. At the 4th stage the upper extract phase (about 93 g) contained 0.2% w/w of citric acid and about 5.6% w/w of amine and the lower extract phase (about 65 g) contained about 19.5% w/w of citric acid and about 48% of amine. The two extract phases were handled together and were stripped at 100° C. in a single stage with 60 g of $H_2O$ to yield about 73 g of a back-extract containing about 2.7 g of citric acid i.e. a concentration of 17.5% w/w of citric acid. At the same time 145 g of an homogeneous organic extractant phase was obtained, which was ready to recycle after cooling.

EXAMPLE 5

100 g of an 18% w/w crude citric acid broth were extracted at 40° C. in five counter-current stages (simulated by five separatory funnels) with 220 g of recycled extractant containing 34% w/w of trilauryl amine, 5% w/w of dilauryl amine, 53% w/w of a petroleum fraction boiling at 180°–210° C., 5% w/w of 1-n-octanol and 3% w/w of citric acid. The aforesaid mixture of trilaurylamine and dilaurylamine is a commercial product. The extract amounted to 237 g and contained 10% of citric acid. It was stripped at 65° C. in five simulated counter-current stages with 96 g of $H_2O$ to yield 113 g of an aqueous back-extract containing 15% w/w of pure citric acid. At the same time 220 g of extractant phase was obtained which was ready for recycle after cooling.

The presence of the 1-n-octanol in the extractant prevented the stratification of the extract described in Example 4.

EXAMPLE 6

200 g of a 10% w/w crude citric acid broth were extracted at 25° C. in three counter-current stages (simulated by three separatory funnels) with 230 g of an extractant containing 36% w/w of trilaurylamine, 57% w/w of a petroleum fraction boiling at 180°–210° C., and 5% w/w of octanol. The extract amounted to 250 g and contained 8% w/w of citric acid.

One-half of the extract (125 g) was stripped at 40° C. in four simulated counter-current stages with 90 g of H₂O to yield 96 g of a back-extract containing 6 g of pure citric acid i.e. a purified aqueous solution containing 6% w/w of citric acid, which amounted to a 60 percent recovery.

The other half of the extract (125 g) was stripped similarly but at 60° C., and yielded 100 g of a back-extract containing about 10 g of pure citric acid; i.e. a purified aqueous solution containing about 10% w/w of citric acid, which was a substantially 100 percent recovery.

This Example showed that with a temperature interval of 35° C. between the extraction and back-extraction stages the back-extraction was more complete than with a temperature interval of 15° C. only.

EXAMPLE 7

100 g of a 10% w/w crude citric acid broth was contacted in a separatory funnel at room temperature with 100 g of an extractant containing 50% w/w of tri-tridecylamine and 50% w/w of nitrobenzene. After shaking and phase separation it was found that over 90% of the citric acid had transferred to the extract which thus contained 9.3% w/w of citric acid. This extract was treated in two steps.

First 100 g water was added to the extract at 60° C. Only 13% of the initial citric acid was thus back-extracted and the back-extract contained 1.3% w/w of citric acid. Then 150 g of low-boiling hydrocarbon fraction with a boiling temperature of 60°–90° C. was added to the extract, whereby the citric acid concentration in the back-extract increased to 7.5% w/w. Thus the amount of back-extracted citric acid was 7.5 g which corresponded to a 75% recovery in a single contact.

This Example showed that though nitrobenzene was a good extractant solvent, the extract could not readily be back-extracted unless a hydrocarbon fraction was added to it.

EXAMPLE 8

The extraction of crude citric-acid broth was carried out as described in Example 2. The extract, amounting to 136 g and containing 12% w/w of citric acid, was stripped at 80° C. in a single stage with 12.5 g of H₂O. The aqueous back-extract amounted to 17 g and contained 4.5 g of pure citric acid. The residual citric acid remaining in the extract (which at this stage amounted to 131.5 g) was then back-extracted with 18.5 g of a 40% w/w aqueous NaOH solution. All the residual citric acid was thus converted into trisodium citrate. This salt can be recovered from the aqueous solution in a highly pure state (yield 16 g).

EXAMPLE 9

The extraction of crude citric-acid broth and the single-stage stripping of the extract were carried out as described in Example 8. The residual citric acid remaining in the solvent-amine phase (which latter amounted to 131.5 g) was back-extracted in two counter-current stages with 14 g of a 26% w/w aqueous NaCl solution, whereby the residual citric acid was transferred as monosodium citrate into the aqueous phase and the amine in the organic phase was converted into its hydrochloride. The organic phase was treated with an aqueous slurry of Ca(OH)₂ whereby the amine was liberated. The calcium chloride solution was discarded as waste.

EXAMPLE 10

A bench-scale unit was set up comprising an extraction solution of four mixer-settlers units, and a stripping section of four mixer-settler units. The mixer-settler units corresponded to those described in the U.S. Pat. No. 3,489,526, their dimensions being adapted to the quantities of liquid to be processed in accordance with this Example. The four units of the stripping sections were provided with hot-water coils to permit operation at temperature around 80° C.

The extraction section was fed in counter-current with 1000 g/hr (900 ml/hr) of crude citric acid broth containing 15.7% w/w of citric acid, and 1500 g/hr (1800 ml/hr) of an extractant composed of a 40% w/w solution of technical-grade trilaurylamine in a petroleum fraction (boiling range 140°–210° C.) containing 3-5% by weight of 1-n-octanol. When steady state was attained the extract, 1655 g/hr (1800 ml/hr) containing 9.9% w/w of citric acid, was fed through a preheater to the stripping section where the temperature was maintained at 80° C. Hot water was fed at a rate of 360 ml/hr to the stripping section in counter-current to the extract for stripping the citric acid from the extract. When steady state was attained the back-extract contained 28% w/w of pure citric acid. The stripped extractant was cooled and recycled to the extraction section. The aqueous back-extract was evaporated whereby pure crystalline citric acid was recovered.

EXAMPLE 11

100 g of the aqueous wash liquor obtained by washing a crude citric acid filter cake and containing 5% w/w of citric acid was extracted with 30 g of a mixture of 1:1 w/w, of Amberlite LA-1 (trade name of a liquid secondary amine containing 23–26 C atoms) and the same petroleum fractions as used in Example 4. The extraction was effected at room temperature in three stages in a separatory-funnel simulation of a counter-current extraction. The extract was contacted in four stages with 25 ml of water at 90° C., whereby an aqueous back-extract containing 15% w/w of citric acid was obtained.

EXAMPLE 12

100 g of a crude dilute aqueous lactic acid liquor containing 2% w/w of lactic acid was contacted in three counter-current stages with 40 g of an extractant composed of 50% w/w of tri-tridecylamine and 50% w/w of 1-n-octanol. The extract was stripped with 40 g of water at a temperature near its boiling point in five counter-current stages. About 2 g of free lactic acid was obtained as a 5% w/w aqueous solution.

EXAMPLE 13

100 g of a 10% w/w aqueous lactic acid solution was extracted in a separatory funnel simulation of a two-stage counter-current extraction system with 130 g of an extractant consisting of 50% w/w of trioctylamine and 50% w/w of a petroleum fraction boiling at 140°–210° C. The extract, containing 7.5% of lactic acid, was stripped with 54 g of water in a similar three-stage counter-current system at 80° C. The aqueous back-extract amounted to about 63 g and contained about 9.5 g of pure lactic acid.

EXAMPLE 14

100 g of an 8% w/w aqueous $H_3PO_4$ solution was extracted with a mixture of trilaurylamine (40% w/w) and a petroleum fraction boiling at 140°–210° C. (60% w/w) in a three-stage counter-current system at 25° C. 130 g of extract, containing 6% w/w of $H_3PO_4$, was obtained. The extract was stripped with 20 g of water at 80° C. in three counter-current stages. The back-extract consisted of about 28 g of 25% w/w of pure aqueous $H_3PO_4$.

EXAMPLE 15

Crude citric-acid broth from the citric acid fermentation of sucrose may contain some oxalic acid. In the process according to the invention the oxalic acid is coextracted with the citric acid, but is not stripped from the extract and does not contaminate the citric acid. On the other hand the accumulation of oxalic acid in the solvent-amine solution is undesirable.

In order to lower the oxalic-acid content of the extractant the latter, after being stripped of the citric acid, is contained with water at 120°–160° C. and under pressure. A part of the oxalic acid is thus back-extracted by the water and the extractant can be recycled without accumulation of oxalic acid. Since the amount of oxalic acid extracted in each extraction operation is small, it is preferred that the removal of oxalic acid from the extractant be done only after at least two extraction and stripping operations.

EXAMPLE 16

100 g of a 2% w/w aqueous solution of oxalic acid was extracted in a separatory funnel with 35 g of an extractant containing 25% w/w dilaurylbenzylamine, 69% w/w of n-octane and 6% w/w of 1-n-octanol. After shaking at 40° C. and phase separation, the aqueous raffinate was substantially free of oxalic acid. The extract contained 5.4% w/w of oxalic acid.

The extract was separated, diluted with a further 50 g of n-octane and heated to 80° C., and back-extracted with 30 g water heated to the same temperature. The oxalic acid was back-extracted almost completely. The organic extractant phase contained less than about 0.5% w/w oxalic acid.

We claim:

1. A process for the recovery of an acid selected from the class consisting of citric acid, lactic acid, oxalic acid and phosphoric acid from an aqueous solution of the same acid comprising the steps of subjecting such aqueous acid solution to extraction with a water-immiscible organic extractant which comprises a solution of at least one secondary or tertiary amine in which the aggregate number of carbon atoms is at least 20 and a water-immiscible organic solvent selected from the class consisting of aliphatic hydrocarbons, aromatic hydrocarbons, petroleum fractions, hydrocarbons carrying nitro or halo substituents, alcohols and mixtures thereof to form an organic extract; subjecting the organic extract to a stripping operation with an aqueous liquid at a temperature higher than the temperature at which the extraction is performed for back-extracting at least a substantial part of the acid from the organic extract into the aqueous liquid and leaving substantially all the amine in the organic phase, and separating the aqueous back-extract from the stripped organic extractant.

2. The process of claim 1, wherein the stripping operation is performed at a temperature of at least 20 degrees (centigrade) above the extraction temperature.

3. The process of claim 2, wherein the extraction operation is performed at room temperature and the stripping operation is performed at a temperature of about 80° C. or above.

4. The process of claim 1, wherein the stripping operation is carried out under superatmospheric pressure at a temperature above 100° C.

5. The process of claim 1, wherein the extraction operation is performed as a continuous multi-stage counter-current process and the stripped organic extract is cooled to the extraction temperature and recycled to the extraction stage.

6. The process of claim 1, wherein the composition of the organic extract is changed after the extract has been separated from the residual aqueous liquid and before the extract is subject to stripping.

7. The process of claim 6, which comprises removing a part of the organic solvent from the organic extract before the stripping operation.

8. The process of claim 6, which comprises adding an organic solvent to the organic extract before the stripping operation.

9. The process of claim 8, in which the added solvent is the same as the original solvent of the extract.

10. The process of claim 8, in which the added solvent is different from the original solvent of the extract.

11. The process of claim 6, in which the composition of the stripped extract is substantially reconstituted to the original composition of the extractant and the reconstituted extractant is recycled to the extraction stage.

12. The process of claim 1, for preparing an alkali metal (including ammonium) salt of the extracted acid, comprising using an aqueous alkali metal (including ammonium) hydroxide or salt solution as the aqueous liquid for at least a part of the back-extracting operation.

13. The process of claim 12, wherein the organic extract is first contacted with water for the back-extraction of a part of the extracted acid in the free state, and thereafter with an aqueous solution of an aqueous alkali metal (including ammonium) hydroxide or salt for the back-extraction of the remainder of the extracted acid in the form of its alkali metal (including ammonium) salt.

14. The process of claim 1, wherein citric acid is recovered from an aqueous solution of citric acid.

15. The process of claim 14, wherein the aqueous solution of citric acid is crude citric acid fermentation broth.

16. The process of claim 15, wherein crude citric acid fermention broth containing citric acid as a main fermentation product and oxalic acid as a by-product is submitted to extraction with a water-immiscible organic extractant which comprises a solution of at least one secondary or tertiary amine in which the aggregate number of carbon atoms is at least 20 and a water-immiscible organic solvent selected from the class consisting of aliphatic hydrocarbons, aromatic hydrocarbons, petroleum fractions, hydrocarbons carrying nitro or halo substituents, alcohols and mixtures thereof to form an organic extract; the organic extract is separated from the residual aqueous liquid; the organic extract is subjected to a stripping operation with an aqueous liquid at a temperature higher than the temperature at which the extraction is performed for back-extracting at least a substantial part of the citric acid from the organic extract into the aqueous liquid and leaving at least the major part of the oxalic acid and substantially all the amine in the organic phase; the aqueous back-extract is separated from the stripped organic extractant; the extractant is recycled to the extraction stage; and after at least two extraction and stripping operations the stripped extractant is freed from at least part of the oxalic acid accumulated therein.

17. The process of claim 16, wherein the stripped extractant is contacted with water under pressure at a temperature of from 120° to 160° for freeing it from at least part of the oxalic acid contained therein.

18. The process of claim 1, in which the water-immisicible organic solvent is selected from the class consisting of xylene, a petroleum fraction having a boiling temperature range of about 140° C. to 210° C., a petroleum fraction having a boiling temperature range of about 180° C. to 210° C., octanol, nitrobenzene, octane, and mixtures thereof.

19. The process of claim 1, in which the amine is selected from the class consisting of tri-tridecylamine, trilaurylamine, trioctylamine, dilaurylamine, a liquid secondary amine containing 23 to 26 C atoms, a dilaurylbenzylamine, tricaprylylamine, and mixtures thereof.

* * * * *